United States Patent
Guo et al.

(10) Patent No.: US 9,378,548 B2
(45) Date of Patent: Jun. 28, 2016

(54) $T_2$ SPECTRAL ANALYSIS FOR MYELIN WATER IMAGING

(71) Applicant: ST. JUDE CHILDREN'S RESEARCH HOSPITAL, Memphis, TN (US)

(72) Inventors: Junyu Guo, Memphis, TN (US); Wilburn E. Reddick, Bartlett, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 153 days.

(21) Appl. No.: 14/359,722

(22) PCT Filed: Nov. 29, 2012

(86) PCT No.: PCT/US2012/066935
§ 371 (c)(1),
(2) Date: May 21, 2014

(87) PCT Pub. No.: WO2013/082207
PCT Pub. Date: Jun. 6, 2013

(65) Prior Publication Data
US 2014/0270453 A1 Sep. 18, 2014

Related U.S. Application Data

(60) Provisional application No. 61/565,578, filed on Dec. 1, 2011.

(51) Int. Cl.
*G06K 9/00* (2006.01)
*G06T 7/00* (2006.01)
*G06T 5/00* (2006.01)
*G01R 33/50* (2006.01)
*G01R 33/483* (2006.01)

(52) U.S. Cl.
CPC .............. *G06T 7/0012* (2013.01); *G01R 33/50* (2013.01); *G06T 5/002* (2013.01); *G01R 33/4835* (2013.01)

(58) Field of Classification Search
None
See application file for complete search history.

(56) References Cited

U.S. PATENT DOCUMENTS

2009/0312625 A1 12/2009 Du
2010/0142784 A1 6/2010 Yarnykh

OTHER PUBLICATIONS

International Search Report and Written Opinion in related PCT Application No. PCT/US12/66935, filed Nov. 29, 2012; Notification Date Feb. 13, 2014.
Craig K. Jones; "T2 Decay Curve Acquisition and Analysis in MRI, Noise Considerations, Short T2, and B1 Field Encoding", Dept. of Physics and Astronomy, University of BC, Jul. 31, 2003, pp. 1-161.
Sarlls et al.; "Diffusion-Weighted Radial Fast Spin-Echo for High-Resolution Diffusion Tensor Imaging at 3T", National Institute of Health, Magnetic Resonance in Medicine 60, pp. 270-276, (2008).

*Primary Examiner* — Atiba O Fitzpatrick
(74) *Attorney, Agent, or Firm* — Eschweiler & Associates, LLC

(57) ABSTRACT

Apparatus, methods, and other embodiments associated with the spectral analysis of $T_2$ spectral data are described. One example magnetic resonance imaging (MRI) method includes accessing a data set comprising $T_2$ spectral data associated with a magnetic resonance imaging (MRI) signal received from an object. The $T_2$ spectral data is decomposed with multi-exponential functions to determine $T_2$ spectra. The $T_2$ spectral amplitude is regularized with a regularized constant. The regularized constant is sufficiently large to smooth the $T_2$ spectra so adjacent pixels of the $T_2$ spectral data have similar characteristics. The $T_2$ spectral data is weighted so that the regularization is uniformly weighted for the spectral amplitudes. The $T_2$ spectra is partitioned into intervals corresponding to myelin water fraction (MWF), tissue water fraction (TWF), Long T2 water fraction (LWF), and cerebrospinal fluid fraction (CSF). Parametric maps are generated based, at least in part, on the $T_2$ spectral data.

17 Claims, 12 Drawing Sheets

US 9,378,548 B2

$T_2$ SPECTRAL ANALYSIS FOR MYELIN WATER IMAGING

CROSS REFERENCE TO RELATED APPLICATIONS

This patent disclosure is a National Entry from PCT Application No. PCT/US12/66935 filed on Nov. 29, 2012, which claims the benefit of U.S. Provisional Application No. 61/565,578 filed on Dec. 1, 2011, which is hereby wholly incorporated by reference.

BACKGROUND

MRI is a diagnostic imaging technique in which image contrasts may be generated. Different image contrasts may be sensitive to different pathologies. Two image contrasts for diagnostic medicine are $T_1$ contrast and $T_2$ contrast. $T_2$ contrast corresponds to the rate at which magnetization disappears perpendicular to the main magnetic field. $T_2$ contrast is useful in clinical imaging. $T_2$ contrast is often used to facilitate identification of tumors, tissue affected by stroke and other lesions, pathologies, and other differences between normal and diseased tissue.

For example, damaged myelin can be distinguished from undamaged myelin based on differences in the $T_2$ decay. One type of damage to myelin, referred to as demyelination, impairs the conduction of signal for an affected neuron. In addition to causing degradation of a neuron's signal, demyelination results in bundle migration. Bundle migration refers to the distance between nerve fibers in a nerve bundle. Some brain diseases including multiple sclerosis (MS), leukoencephalopathy (LE), are related to loss of myelin water (MW). Myelin water fraction (MWF) can serve as a direct indicator of myelin integrity and provide quantitative measurements of myelin structure and change due to white matter diseases.

$T_2$ contrast is typically generated using a spin-echo (SE) or turbo-spin-echo (TSE) sequence. A single spin-echo is formed through a combination of a 90 degree pulse and a 180 degree pulse. The 90 degree pulse generates signal perpendicular to the main magnetic field and is followed by the 180 degree pulse that refocuses transverse magnetization to form an echo. A purely $T_2$ weighted spin echo signal may be acquired at a point in time after the 180 degree pulse. The time at which the echo is acquired, the echo time (TE), occurs at a time after the 180 degree pulse that is equal to the spacing between the 90 degree pulse and the 180 degree pulse.

Conventionally, a $T_2$ decay curve may be measured using a single-slice multi-echo Carr-Purcell-Meiboom-Gill (CPMG) sequence with nonselective composite refocusing pulses and large z-axis gradient crushers. However, the single-slice coverage, long acquisition time (e.g., 25 minutes) due to nonselective refocusing pulses, and increasing signal-to-noise ratio (SNR) are obstacles to practical clinical applications. To increase volume coverage, a conventional multi-slice CPMG sequence with slice-selective refocusing pulse may be used. However, due to intrinsic sensitivity to refocusing imperfection, the measured curve deviates from the true $T_2$ decay curve, which may be pronounced for the first several points.

In another conventional method, a $T_2$ preparation spiral imaging sequence is used. However, this method yielded MWF maps with low resolution and poor image quality. Multi-slice techniques based on $T_2^*$ signal decay have also been proposed to achieve larger volume coverage and shorter acquisition time. However, high sensitivity to local field inhomogeneity is a limitation of this technique for practical applications since local field gradient along a slice direction can introduce non-exponential signal decay. Furthermore, a signal void region is observed in MWF maps even when high-order shim is performed to minimize field inhomogeneity before data acquisition and the correction of field inhomogeneity is performed in the post-processing.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DEFINITIONS

Figure 1:
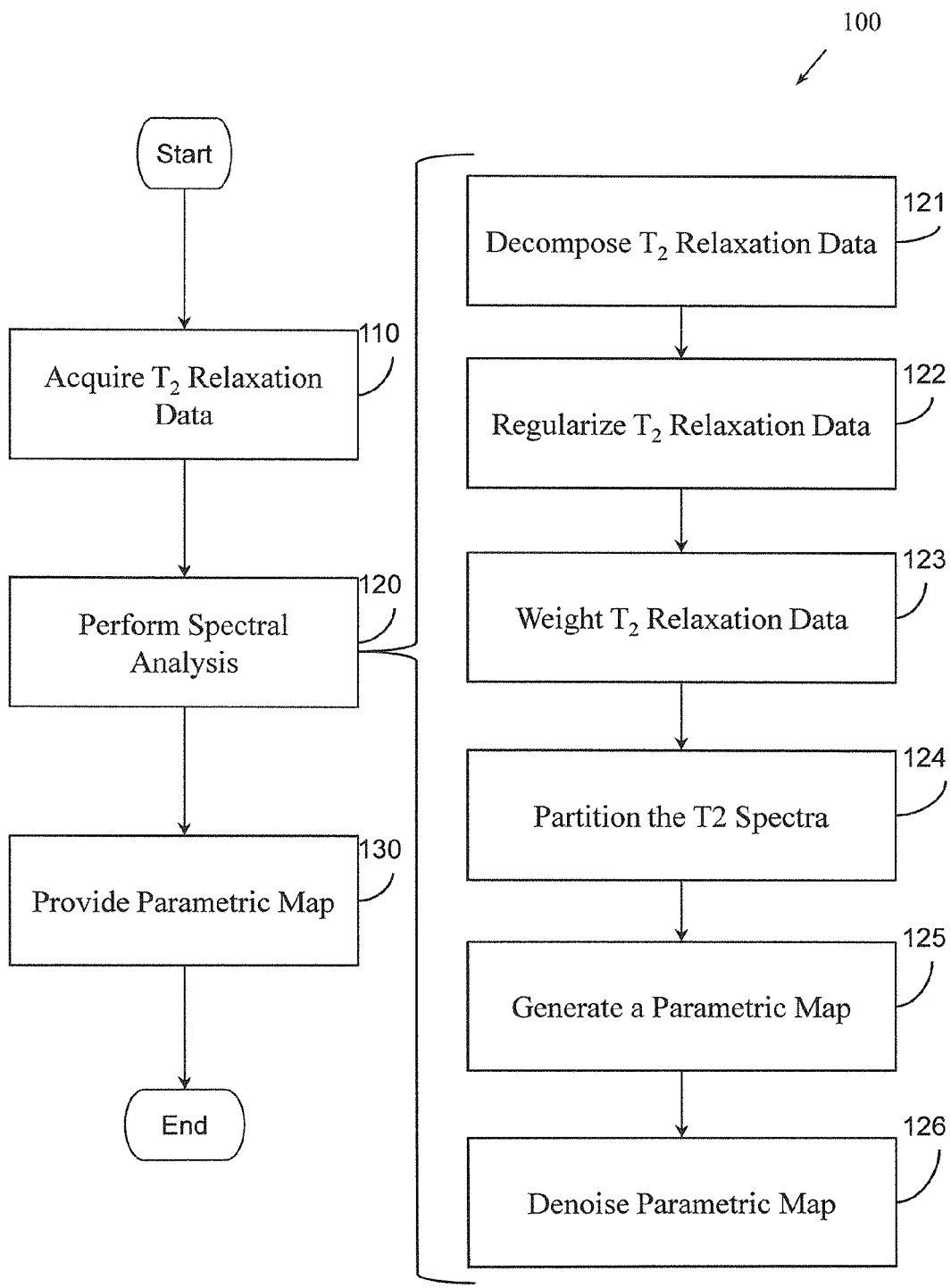
FIG. 1 illustrates a method associated with the spectral analysis of $T_2$ spectral data.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable medium", as used herein, refers to a non-transitory medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

"Logic", as used herein, includes but is not limited to hardware, firmware, software and/or combinations thereof to perform a function(s) or an action(s), and/or to cause a function or action from another logic, method, and/or system. Logic may include a software controlled microprocessor, discrete logic (e.g., application specific integrated circuit (ASIC)), an analog circuit, a digital circuit, a programmed logic device, a memory device containing instructions, and so on. Logic may include a gate(s), a combinations of gates, other circuit components, and so on. In some examples, logic may be fully embodied as software. Where multiple logical logics are described, it may be possible in some examples to incorporate the multiple logical logics into one physical logic. Similarly, where a single logical logic is described, it may be possible in some examples to distribute that single logical logic between multiple physical logics.

"Software", as used herein, includes but is not limited to, one or more computer instructions and/or processor instructions that can be read, interpreted, compiled, and/or executed by a computer and/or processor. Software causes a computer, processor, or other electronic device to perform functions, actions and/or behave in a desired manner. Software may be embodied in various forms including routines, algorithms, modules, methods, threads, and/or programs. In different examples software may be embodied in separate applications and/or code from dynamically linked libraries. In different examples, software may be implemented in executable and/or loadable forms including, but not limited to, a stand-alone program, an object, a function (local and/or remote), a servelet, an applet, instructions stored in a memory, part of an operating system, and so on. In different examples, computer-readable and/or executable instructions may be located in one logic and/or distributed between multiple communicating, co-operating, and/or parallel processing logics and thus may be loaded and/or executed in serial, parallel, massively parallel and other manners.

Suitable software for implementing various components of example systems and methods described herein may be developed using programming languages and tools (e.g., Java, C, C#, C++, SQL, APIs, SDKs, assembler). Software, whether an entire system or a component of a system, may be embodied as an article of manufacture and maintained or provided as part of a machine-readable medium.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

DETAILED DESCRIPTION

Myelin is a major substance of the white matter in human brain. Myelin forms an electrically insulating layer to support and protect the axon of a neuron for the proper functioning of the nervous system. Myelin water is quantified with a multi-interval analysis of a $T_2$ spectrum from a $T_2$ decay curve. The intervals in human brain may include (1) myelin water, having a $T_2$ component with a $T_2$ range from 15 to 40 ms at 3.0 T; (2) tissue water, having a $T_2$ component with a $T_2$ range from 40 to 200 ms; (3) long $T_2$ tissue water, having a $T_2$ component with a $T_2$ range from 200 to 800 ms, and (4) cerebrospinal fluid, having a $T_2$ component with a $T_2$ range from 800 to 2000 ms. The ratios of the components to the summation of the components are termed myelin water fraction (MWF), tissue water fraction (TWF), long $T_2$ tissue water fraction (LWF), and cerebral spinal fluid fraction (CSF).

Example apparatus and methods are associated with the spectral analysis of magnetic resonance imaging (MRI) $T_2$ spectral data associated with myelin. This method is called $T_2$ SPectrum Analysis using a weighted Regularized Approach and non-loCal mean filter ($T_2$SPARC). In one embodiment, a modified multi-slice CPMG sequence is employed with a refocusing slice whose thickness is three times larger than an excitation slice. The size of the refocusing slice is configured with respect to the excitation slice to diminish deviations from the curve. Using a refocusing slice thickness that is three times larger than the excitation slices facilitates achieving a balance between acquisition time and quality of $T_2$ decay curves. Additionally, since SNR affects the quality of MWF maps, in one embodiment, a weighted regularized approach with a large regularization coefficient is used in combination with a non-local mean (NLM) de-noising method to reduce the effect of noise and lessen requirement for the quality of $T_2$ decay curve. While a refocusing slice three times larger than an excitation slice is described, one of ordinary skill in the art will appreciate that other ratios (e.g., 3.1 to 1, 2.9 to 1) between the refocusing slice and the excitation slice may be employed.

FIG. 1 illustrates a method 100 associated with $T_2$ spectral analysis for myelin water imaging. Method 100 includes, at 110, accessing $T_2$ spectral data from an object prepared by a pulse sequence and applied by an MRI apparatus. In one embodiment, the object may be a brain. Ten axial brain slices may be acquired over two scans. The slice position of the second scan may be shifted relative to the first scan so that the first scan and the second scan are interleaved. While ten slices and two acquisitions are described, one of ordinary skill in the art will appreciate that a greater and/or lesser number of slices and a great and/or lesser number of scans may be employed.

In conventional $T_2$ imaging, a first portion of the $T_2$ spectral data is misrepresented due to a portion of the slice not being subject to an adequate refocusing pulse. Deviations in the first portion of the $T_2$ decay curve have a profound effect on the MWF because MWF is derived from the $T_2$ spectral data in the first interval from 15 to 40 ms. Using a modified refocusing pulse with a slice thickness three times larger than the excitation pulse facilitates acquiring initial $T_2$ spectral data with greater accuracy.

Method 100 also includes, at 120, controlling the MRI apparatus to perform a spectral analysis of the $T_2$ spectral data. The spectral analysis includes uniformly weighting the $T_2$ spectral data, using a pre-determined regularization constant, and using $T_2$ spectral component thresholds to define the multiple intervals of myelin water imaging. In one example, the spectral analysis of the $T_2$ spectral data includes, at 121, decomposing the $T_2$ spectral data using multi-exponential functions to produce $T_2$ spectra. The multi-exponential functions may be employed using, for example, a non-negative least squares (NNLS) approach.

To improve the reliability of the result of the multi-exponential functions, the spectral analysis at 120, includes, at 122, regularizing the $T_2$ spectral amplitude by applying a regularized constant μ. Conventionally, a small regularization constant may be used. However, a sufficiently large regularized constant, p, can smoothen the $T_2$ spectra so adjacent pixels of the $T_2$ spectral data have similar characteristics.

If the $T_2$ spectrum is uniformly sampled, the regularization is uniformly weighted for all spectral amplitudes. However, if $T_2$ spectrum is logarithmically sampled, the regularization puts more weight on spectral amplitudes that correspond to larger log-spaced time intervals. The logarithmically sampled weighting disparity is further aggravated the larger the regularized constant, p.

To ameliorate the logarithmically sampled weighting disparity, the example spectral analysis at 120 includes, at 123, weighting the multi-exponential functions. Weighting is performed so that in one example the regularization is uniformly weighted for the spectral amplitudes. The multi-exponential functions may be weighted with an element representative of inverse of log-spaced $T_2$ time intervals. For example, at 123, an inverse of log-spaced $T_2$ time interval matrix may be applied to the multi-exponential functions.

A plurality of $T_2$ spectra result from applying weighted regularized multi-exponential functions to the T2 spectral data. The example spectral analysis 120 includes, at 124, partitioning the $T_2$ spectra into intervals by fixed thresholds. In different examples, the intervals may correspond to MWF, TWF, LWF, and CSF. An individual fraction may correspond to an interval. In another embodiment, the intervals may be defined by determining thresholds.

The example spectral analysis 120 includes, at 125, generating at least one parametric map. For an individual pixel of a plurality of pixels, the ratios of at least one of MW, TW, LW, and CS components to the summation of all components are computed to determine the at least one corresponding to MWF, TWF, LWF, and CSF. The computed value of MWF, TWF, LWF, or CSF for the plurality of pixels may be used to generate the corresponding parametric map.

The example spectral analysis at 120 includes, at 126, denoising the at least one parametric map. In one example, the parametric map may be de-noised with a Non Local Mean (NLM) filter. The NLM filter is applied after the $T_2$ spectral analysis (e.g., wrNNLS). Method 100 also includes, at 130, providing the at least one parametric map.

Figure 2:
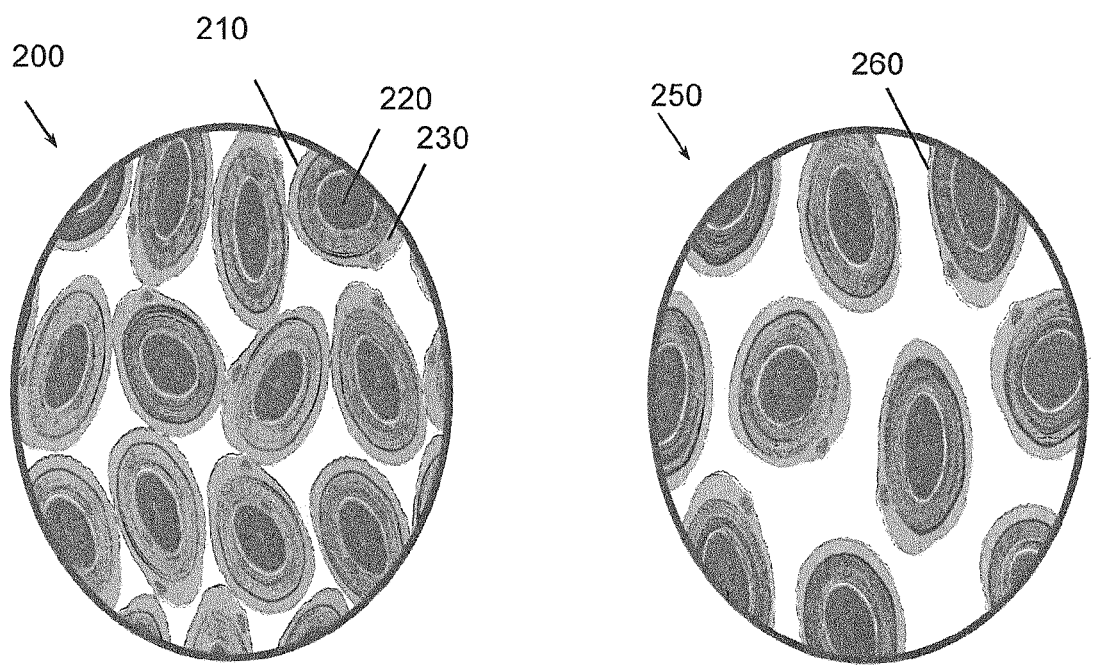
FIG. 2 illustrates an example of a normal nerve bundle and an abnormal nerve bundle.

The method 100, as illustrated in FIG. 1, may be used to measure myelin water in white matter. FIG. 2 illustrates an example of normal white matter 200 and abnormal white matter 250. The white matter 200 comprises a plurality of nerve fibers. A nerve fiber 210 has an axon 220. The axon 220 is an extended fiber of a nerve cell that carries a nerve signal. The axon 220 is surrounded by myelin 230. In normal white matter 200 the nerve fibers are grouped closely together. In abnormal white matter 250, the nerve fibers, such as nerve fiber 260, are not grouped together. Instead, the nerve fibers are subject to bundle migration, meaning the nerve fibers are moving away from one another.

Figure 3:
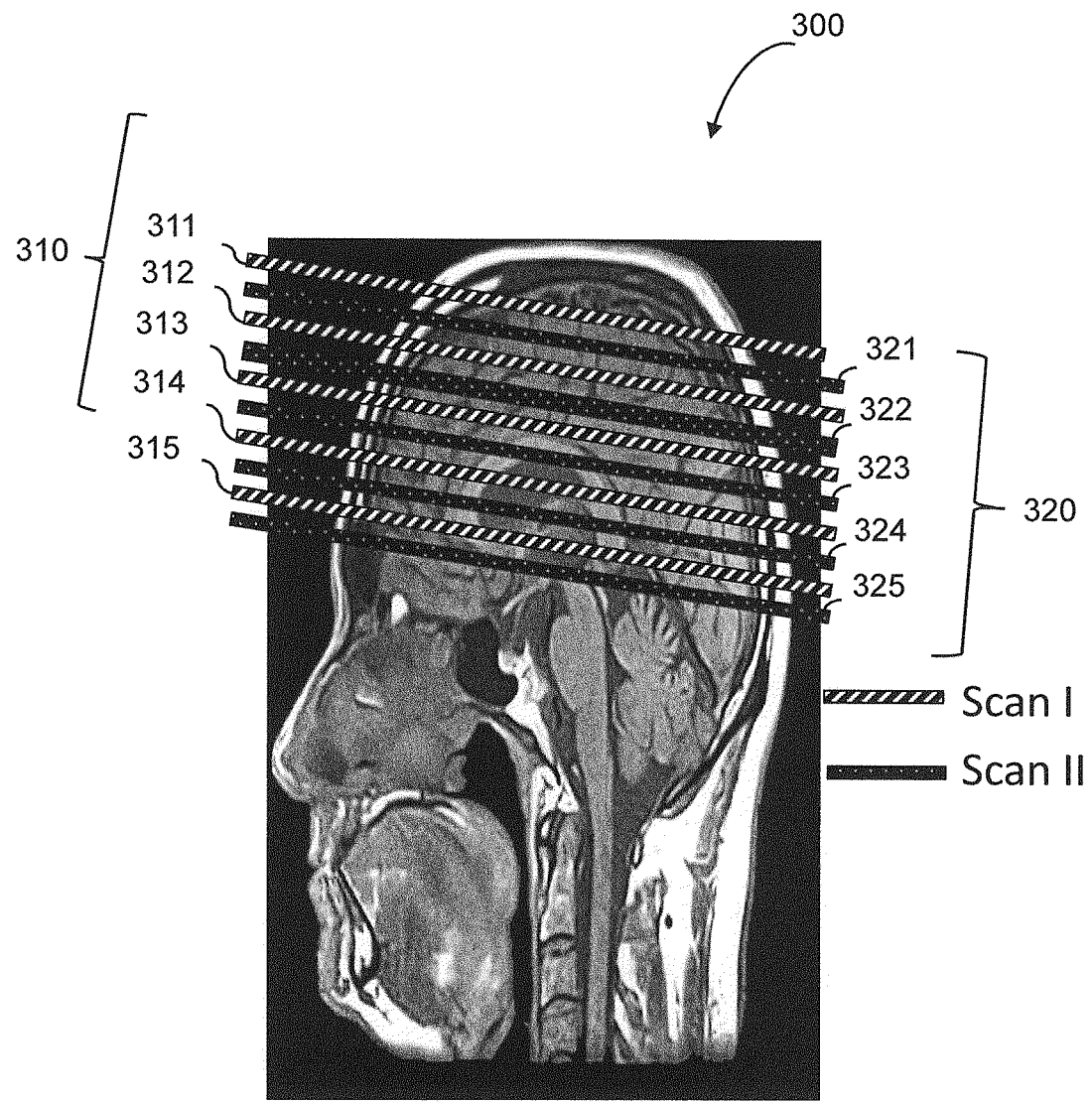
FIG. 3 illustrates an example data acquisition scheme with respect to the spectral analysis of $T_2$ spectral data.

FIG. 3 illustrates an example data acquisition scheme 300 associated with the acquisition of $T_2$ spectral data. In one example, a total of ten brain axial slices from two scans may be acquired using a modified pulse sequence on a 3T scanner using 12-channel head coil. A first scan 310 that includes five axial brain slices 311, 312, 313, 314, and 315 is performed. Subsequently, a second scan 320 that also includes five axial brains slices 321, 322, 323, 324, and 325 is performed. In the example, the individual brain axial slices of the ten brain axial slices have a slice thickness of 5 mm. The slice position of the second scan 320 is shifted 7.5 mm relative to the first scan 310 to form two interleaved scans of ten consecutive slices with 2.5 mm gap. One of ordinary skill in the art will appreciate that greater and/or lesser number of scans may be employed and that different slice shifts and different slice thicknesses may be employed.

The imaging protocol for the two scans in the example may include: FOV=220×220 mm; slice thickness=5 mm; acquisition matrix=256×256; 5 slices with 200% slice gap; TEs=10·N, (N=1, 2, 3, . . . , 32); TR=3000 ms; receiver bandwidth=300 Hz/pixel; GRAPPA reduction factor=2 and the reference line=24. In the example, the acquisition time for the first scan 310 or the second scan 320 may be 5:29 minutes with a total time of 11 minutes.

Figures 4A, 4B:
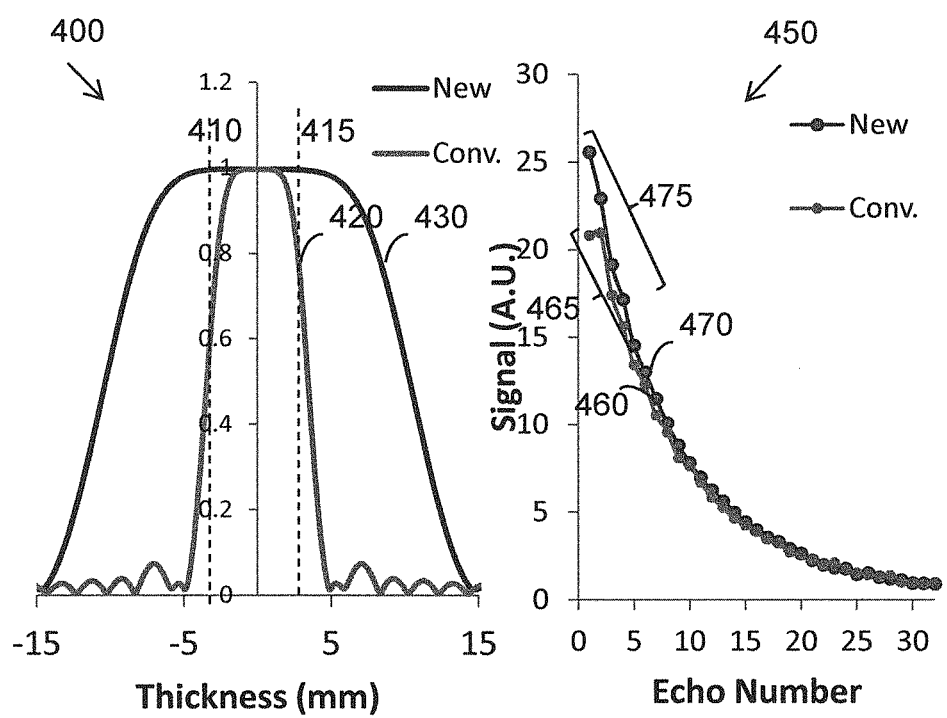
FIG. 4A illustrates example refocusing slice profiles associated with $T_2$ spectral data acquisition.
FIG. 4B illustrates example $T_2$ decay curves representative of acquired $T_2$ spectral data.

FIG. 4A illustrates a graph 400 associated with the thickness of refocusing slice profiles. Once the number of scans and slices is established based on the imaging protocol, a pulse sequence is determined. Imperfections in the conventional refocusing slice profile 420 contribute to flawed $T_2$ spectral data. A modified pulse sequence with a modified refocusing profile 430 reduces signal deviations as compared to conventional refocusing slice profile 420.

An excitation slice thickness is demarcated by dashed lines 410 and 415. In one embodiment the excitation slice thickness is 5 mm. A conventional refocusing RF pulse has a conventional refocusing slice profile 420. Specifically, there is a significant amount of excitation slice, demarcated by dashed lines 410 and 415, with a refocusing pulse less than 180°. This imperfection leads to large deviations of the first several points in $T_2$ decay curve. The first several points are significant to MWF data since the $T_2$ spectrum corresponding to myelin water is measured in the first interval from 15-40 ms.

A modified refocusing profile 430 increases the slice thickness of the refocusing RF to be larger than the excitation slices demarcated by dashed lines 410 and 415. When the slice thickness of the refocusing RF is larger then the excitation slice, then it may be possible to generate more accurate $T_2$ spectral data. The increased slice thickness of the modified refocusing profile 430 reduces signal deviations. The slice thickness of the modified refocusing slice profile 430 may be three times larger than an excitation slice thickness.

FIG. 4B illustrates a conventional measured $T_2$ decay curve 460 as compared to a modified $T_2$ decay curve 470. Due to intrinsic sensitivity to refocusing imperfections, a conventional measured $T_2$ decay curve 460 deviates from the modified $T_2$ decay curve 470, as illustrated for a first portion 465 of the conventional measured $T_2$ decay curve 460. Previous attempts to ameliorate the conventional refocusing profile 420, as shown in FIG. 4A, have included the addition of constant slice crushers around each refocusing pulse. However, initial values of the first portion 465 of the conventional measured $T_2$ decay curve 460 were still underestimated.

The modified refocusing slice profile 430 leads to a substantially ameliorated $T_2$ decay curve 470 with a corrected first portion 475. Accordingly, the first portion 475 of the ameliorated $T_2$ decay curve 470 yields improved $T_2$ spectrum corresponding to myelin water measured in the first interval from 15-40 ms. Thus, the modified pulse sequence yields more accurate $T_2$ spectral amplitude(s) corresponding to myelin water.

Figure 5:
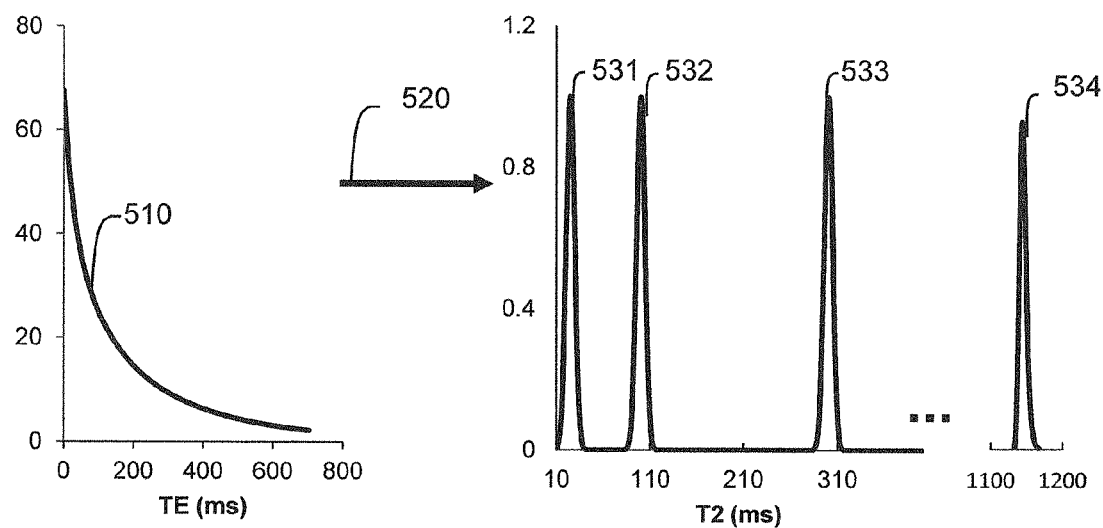
FIG. 5 illustrates graphs associated with a $T_2$ decay curve and $T_2$ spectral peaks.

FIG. 5 illustrates example graphs associated with a $T_2$ decay curve and $T_2$ spectral peaks. The $T_2$ spectral data was acquired from two scans of five axial brain slices acquired using a pulse sequence with a modified refocusing slice profile. The data yields a $T_2$ decay curve 510. Spectral peaks 531, 532, 533, and 534 of the spectral graph 530 are determined using spectral analysis 520.

$T_2$ decay signal, $y(t_n)$, of the $T_2$ decay curve 510, can be described using a general integral of exponential functions:

$$y(t_n) = \int_0^{T_{max}} S(T_2) e^{-\frac{t_n}{T_2}} dT_2, n = 1, 2, \ldots, N \qquad (1)$$

where $t_n$ is the measured time point equal to $n \cdot TE$, and TE is time of echo; $S(T_2)$ is the amplitude of the spectral component at relaxation time $T_2$. The range of $T_2$ is from zeros to maximum $T_2$ value $T_{max}$ (e.g., 2 seconds). This integral equation can be discretized as a summation of piecewise amplitude constants over M small ranges of $T_2$:

$$y_n = \sum_{m=1}^{M} S_{Tm} e^{-\frac{t_n}{T_{2m}}}, n = 1, 2, \ldots, N, \qquad (2)$$

where M is the $T_2$ sampling points and $$S_{Tm} = S_m \Delta T_2 \qquad (3)$$

where $\Delta T_{2m}$ is a logarithmic $T_2$ time interval. Equation (4) is in a general matrix form.

$$Y = ES_T, E_{nm} = e^{-\frac{t_n}{T_{2m}}} \qquad (4)$$

The $T_2$ spectrum can be solved from this equation. The $T_2$ spectrum was partitioned into four intervals: myelin water, $T_2$=15-40 ms; tissue water, 40-200 ms; tissue water with long $T_2$ component, 200-800 ms; cerebral spinal fluid, 800-2000 ms.

The spectral amplitudes $S_{Tm}$ are nonnegative. Thus, an approach, for example, Non-Negative Least Squares (NNLS) approach may be used to perform $T_2$ spectrum analysis 520. Regularization is used to improve the reliability of the solution. Therefore, a regularized approach (e.g., regularized Non-Negative Least Squares (rNNLS)) is used to solve equation (4) by minimizing:

$$\chi^2 = \min\{\|ES_T - Y\|_2 + \mu\|S_T\|_2\}, S_T \geq 0 \qquad (5)$$

where $\|\cdot\|_2$ represents the Euclidean norm, and $\mu$ is a regularization constant. The larger the $\mu$ value, the more the $T_2$ spectrum is smoothened. Conventionally, a small value of $\mu$ is used in a typical MWF study to satisfy the constraint of $1.02 \chi_{min}^2 \leq \chi^2 \leq 1.025 \chi_{min}^2$ where $\chi_{min}^2$ is the minimum misfit of a solution (e.g., an NNLS solution). A smaller $\mu$ value has been conventionally used to avoid smoothing of the spectral peaks derived from the measured $T_2$ decay curve because smoothing was viewed as distorting the $T_2$ spectral data. However, due to use of a smaller p, the regularized approach has been sensitive to noise. Therefore, conventionally, four averages in acquisition are used to double the SNR. Having to acquire four averages prolongs the total acquisition time to over 25 minutes for a single slice. This may be an unacceptably long acquisition time.

The regularized term $S_T$ in equation (5) includes the spectral amplitude S and $T_2$ time interval as shown in equation (3). When $T_2$ spectral data is logarithmically sampled, regularization puts more weight on spectral amplitudes that correspond to larger log-spaced time intervals. Therefore, in addition to being regularized, the $T_2$ spectrum amplitude is weighted to ameliorate the problems caused by using logarithmically spaced $T_2$ time intervals. The larger the $T_2$ time interval, the less weighting. With a larger $\mu$ value, weighting can be applied as follows:

$$X^2 = \min\{\|ES_T - Y\|_2 + \mu\|WS_T\|_2\}, \qquad (6)$$

$$W_m = \frac{1}{\Delta T_{2m}},$$

$$S_T \geq 0$$

where W is a weighting matrix and its element is equal to the inverse of log-spaced $T_2$ time intervals. Using equation (6), the spectral amplitudes are equally weighted in regularization even with logarithmically spaced $T_2$ time intervals.

In one example, after the weighted regularized multi-exponential functions are applied, a filter may be applied. In one embodiment, the filter is a non-local mean (NLM) filter. The noise is reduced by averaging a large number of similar pixels regardless of whether they are spatially close or not. The de-noising performance of an NLM filter is designed for the presence of similar image structure in contrast to other classical neighborhood filters such as anisotropic filter and Gaussian filter. Therefore, a NLM filter is suitable to de-noise parametric maps of MWF and TWF since they have a large area with similar pixels. In one embodiment, a NLM filter with degree of filtering and radiuses of search and similarity window equal to 10, 5 and 2, respectively was used to improve image quality after all MWF, TWF, LWF and CSF parametric maps were scaled by multiplying 1000.

Figure 6A:
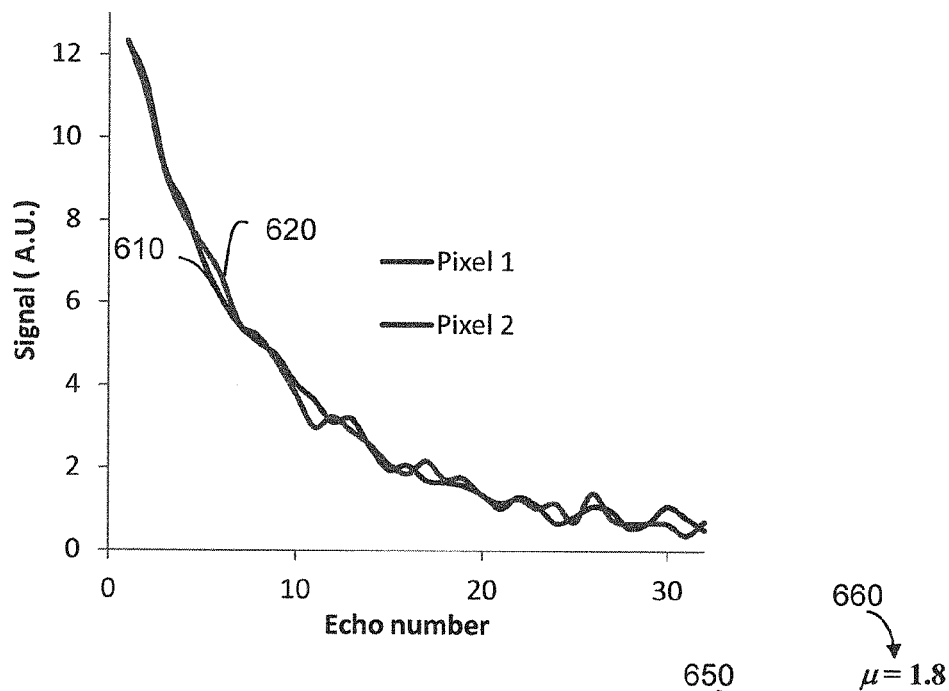
FIG. 6A illustrates $T_2$ decay curves of two adjacent example pixels.

FIG. 6A illustrates $T_2$ decay curves of two adjacent pixels acquired using an example data acquisition scheme. A first $T_2$ decay curve 610 corresponds to a first adjacent pixel. A second T$_2$ decay curve 620 corresponds to a second adjacent pixel. The first and second pixels are located in white matter of the brain and have similar characteristics due to their proximity. Therefore, two adjacent pixels should have approximately the same T$_2$ spectra despite any differences in the amount of noise to which the adjacent pixels are subjected.

Figure 6B:
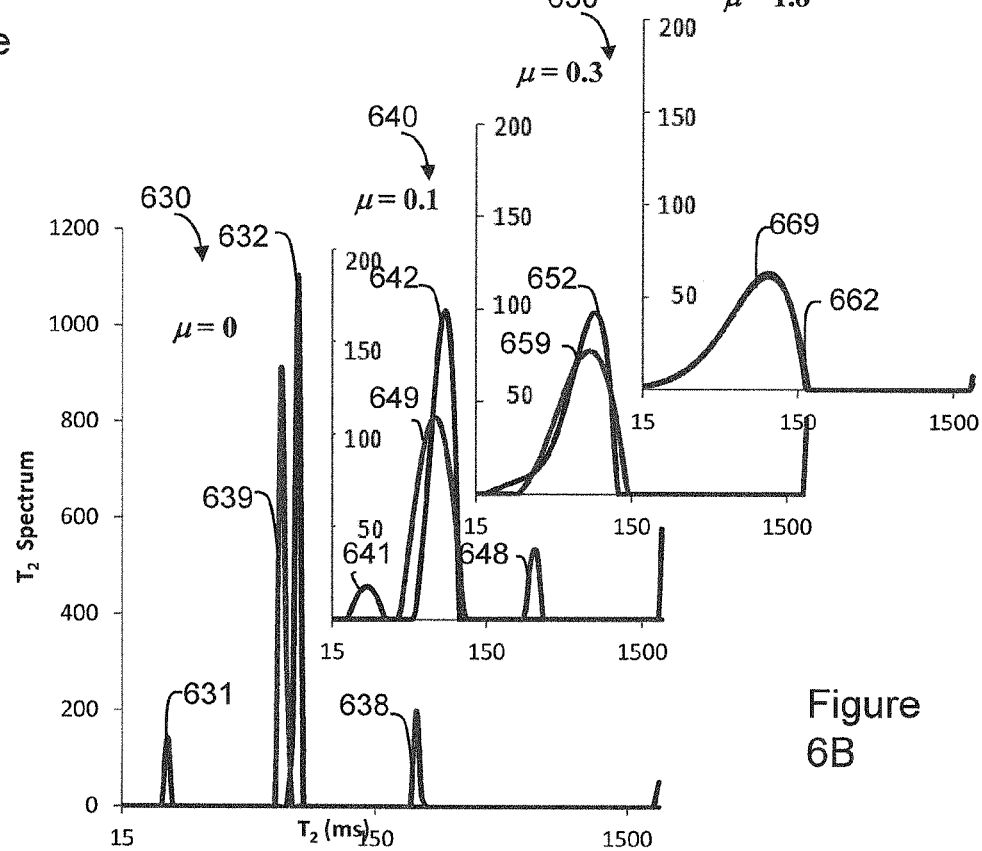
FIG. 6B illustrates the smoothing of $T_2$ spectral data with varying values of the regularization constant, p.

FIG. 6B illustrates the smoothing of T$_2$ spectral data with varying values of the regularization constant, p. A μ value is determined for the first T$_2$ decay curve 610 (shown in FIG. 6A) of the first adjacent pixel and the of a second T$_2$ decay curve 620 (shown in FIG. 6A) of the second adjacent pixel. The first T$_2$ decay curve 610 and the second T$_2$ decay curve 620 are converted to T$_2$ spectra using the weighted regularized approach (e.g., wrNNLS) described with respect to FIG. 5.

The μ=0 graph 630 illustrates the spectral amplitudes of two adjacent pixels. The first pixel spectral peak corresponds to a small peak component 631 and a large peak component 632. Likewise, the second pixel spectral peak corresponds to a small peak component 638 and a large peak component 639. The first spectral peak and the second spectral peak and their components are distinct. Therefore, despite the first pixel and the second pixel being adjacent, without a regularization constant (e.g., μ=0) the first pixel spectral peak and the second pixel spectral peak of the μ=0 graph 630 have different spectral characteristics. The small peak components lead to MWF equal to 0% in one pixel and 9.8% in the other pixel. Thus, despite the proximity of the first adjacent pixel and the second adjacent pixel, the un-regularized results show different characteristics.

A regularization constant, p, is applied to smooth the T$_2$ spectra so that adjacent pixels of the T$_2$ spectral data have similar spectral characteristics. In one example, a regularization constant sufficient to achieve a desired uniformity between the T$_2$ spectra (e.g., T$_2$ spectra with 1% deviation) may be applied. Alternatively, a regularization constant sufficient to avoid a threshold difference (e.g., a 1% difference) in a spectral characteristic (e.g., spectral amplitude) between the adjacent pixels may be applied. The μ=0.1 graph 640 illustrates the spectral amplitudes of the two adjacent pixels with a μ=0.1 applied by an example weighted regularized approach (e.g., wrNNLS). The first pixel spectral peak corresponds to a small peak component 641 and a large peak component 642. Likewise, the second pixel spectral peak corresponds to a small peak component 648 and a large peak component 649.

The regularization constant, p, being equal to 0.1 moves the first spectral peak large component 642 closer to the second spectral peak large component 649. The first pixel spectral peak and the second pixel spectral peak are also associated with small peak components. The two small peak components 641 and 648 are located near their respective large peak components. The peaks became broader with a small regularization coefficient μ=0.1, but the first pixel spectral peak small component 641 and the second pixel spectral peak small component 648 are distinct.

A regularized constant is determined to be sufficiently large to smooth the T$_2$ spectra so that adjacent pixels of the T$_2$ spectral data have similar characteristics. Accordingly, when μ is increased to 0.3, as illustrated in the μ=0.3 graph 650, the first pixel spectral peak 652 and the second pixel spectral peak 659 coincide as broad peaks. Furthermore, the small peak components of the first pixel spectral peak and the second pixel spectral peak are subsumed by the broader first pixel spectral peak 652 and the second pixel spectral peak 659. This is indicative of the spectra near white matter and tissue component becoming one broad peak and having at least more similar spectral characteristics.

In μ=1.8 graph 660 the first pixel spectral peak 662 and the second pixel spectral peak 669 are approximately the same. Therefore, when μ is increased to 1.8, the MWFs of both pixels were computed equal to 12.7% and 12.1%, respectively. Thus, as the μ value increases, the sensitivity to measurement noise in the weighted regularized approach decreases. Additionally, the T$_2$ spectrum becomes increasingly smoother. The smoothness (fidelity) of spectrum and the sensitivity to noise are compromised to achieve a result indicative of the first adjacent pixel and the second adjacent pixel having more similar characteristics. Therefore, μ is defined to be sufficiently large to smooth the T$_2$ spectra so that adjacent pixels of the T$_2$ spectral data have characteristics that differ by less than a threshold amount. For example, μ may be defined such that spectral peaks overlap by at least a certain amount (e.g., 85%, 90%, 99%). In another example, μ may be defined to achieve a desired stability of myelin water fraction.

Figure 7:
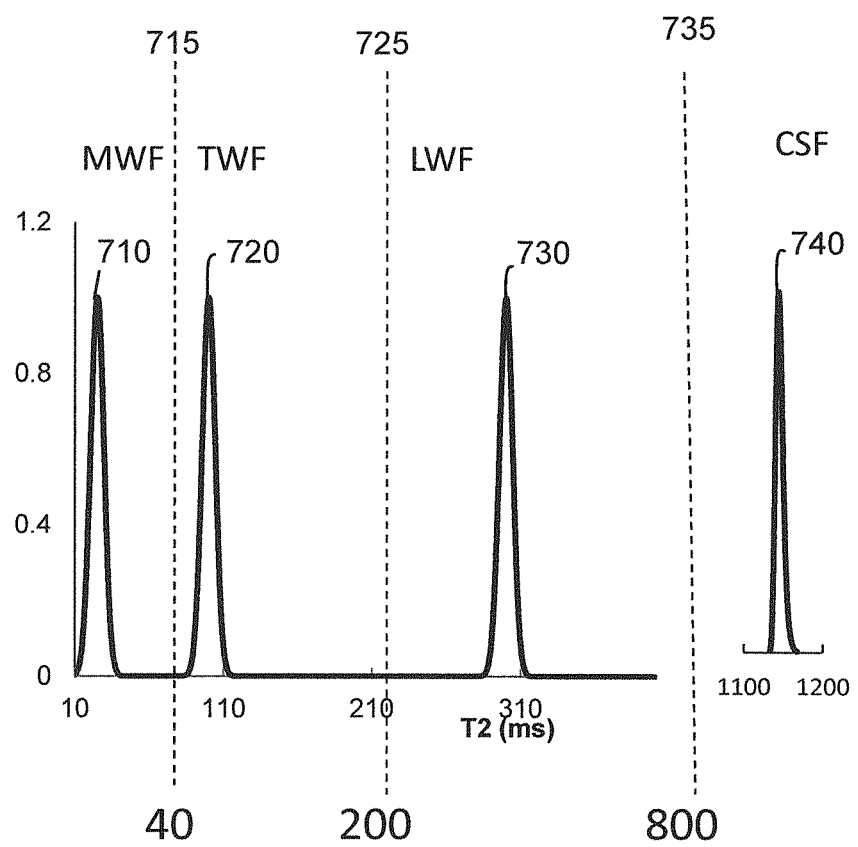
FIG. 7 illustrates example intervals associated with spectral peaks.

FIG. 7 illustrates the spectral components derived from a T$_2$ decay curve. The peaks correspond to components of the T$_2$ decay curve. Specifically, the weighted regularized approach with a predetermined μ value, results in spectral components corresponding to myelin water component 710, tissue water component 720, long T$_2$ tissue water component 730, and cerebrospinal fluid component 740. The ratios of the components to the summation of the components are termed myelin water fraction (MWF), tissue water fraction (TWF), long T$_2$ tissue water fraction (LWF), and cerebral spinal fluid fraction (CSF) respectively.

FIG. 7 illustrates the boundaries of the spectral components. The first boundary 715 separates the myelin water component 710 and the tissue water component 720. The second boundary 725 separates the tissue water component 720 and the long T$_2$ tissue water component 730. The third boundary 735 separates the long T$_2$ tissue water component 730 and the cerebrospinal fluid component 740. Defining the first boundary 715, the second boundary 725, and the third boundary 735 determines which T$_2$ spectral points are used to determine the myelin water component 710, the tissue water component 720, the long tissue water component 730, and the cerebrospinal fluid component 740. Therefore, inaccuracies in the first boundary 715, the second boundary 725, and the third boundary 735 may vary fractions of the myelin water component 710, the tissue water component 720, the long T$_2$ tissue water component 730, and/or the cerebrospinal fluid component 740.

Figure 8:
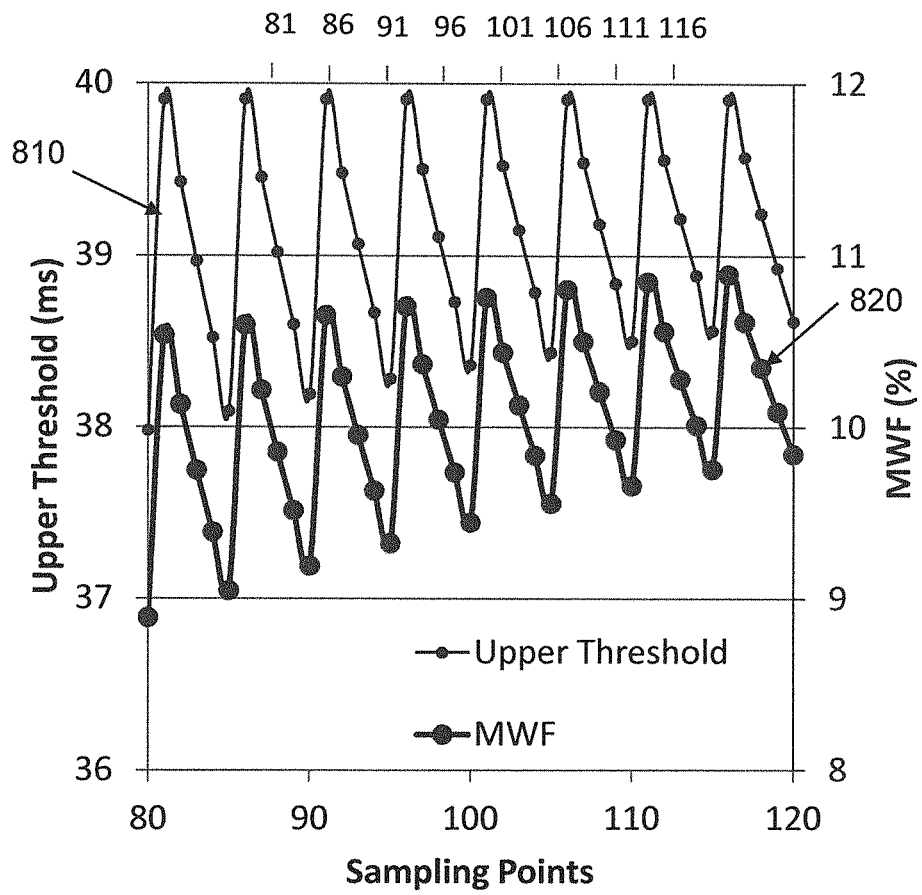
FIG. 8 illustrates example $T_2$ sampling points associated with determining myelin water fraction.

FIG. 8 illustrates the variation of average MWF 820 caused by using different numbers of T$_2$ sampling points 810. Sampling points 810 corresponded to thresholds closest to the specified myelin water T$_2$ threshold 40 ms. Therefore, the number of sampling points and a time interval can be used to determine an appropriate boundary between spectral components. When T$_2$ is logarithmically sampled, the actual upper T$_2$ boundary of myelin water varies with the different number of sampling points 810. In one example, the upper T$_2$ boundary change was consistent with average MWF 820. Thus, the variation of average MWF 820 is caused by using the different number of sampling points 810.

Even with a specified myelin water T$_2$ threshold (e.g. 40 ms), the actual threshold may vary with the number of sampling points 810 and become relevant to the robustness of the wrNNLS approach when T$_2$ is logarithmically sampled. The largest change of MWF was 2%. A change of 2% in MWF is significant since the average MWF is 12%.

Figure 9:
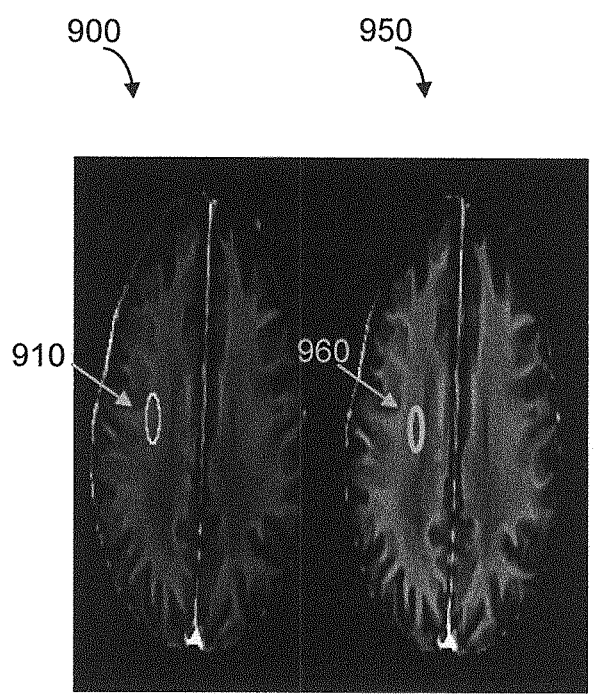
FIG. 9 illustrates an image associated with a conventional refocusing pulse and an image associated with a refocusing pulse that is three times larger.

FIG. 9 illustrates an image associated with conventional refocusing pulses and an image associated with a refocusing pulse that is three times larger. Conventional myelin water fraction (MWF) image 900 was generated from a conventional refocusing profile. Modified MWF image 950 was generated from a modified refocusing profile. Conventional MWF image 900 and modified MWF image 950 are illustrated in the same gray scale.

Conventional MWF image 900 and modified MWF image 950 were generated using the same data processing techniques (e.g., wrNNLS approach with $\mu=1.8$ and $M=96$) and NLM filter. MWF in the conventional MWF image 900 is substantially lower than that in the modified MWF image 950. The average MWF value in a region of interest (ROI) 910 for the conventional MWF image 900 is 5.7%. The average MWF value in a corresponding ROI 960 of the modified MWF image 950 is 11.9%. Therefore, the modified MWF image 950 is more accurate than the conventional MWF image 900.

Figure 10:
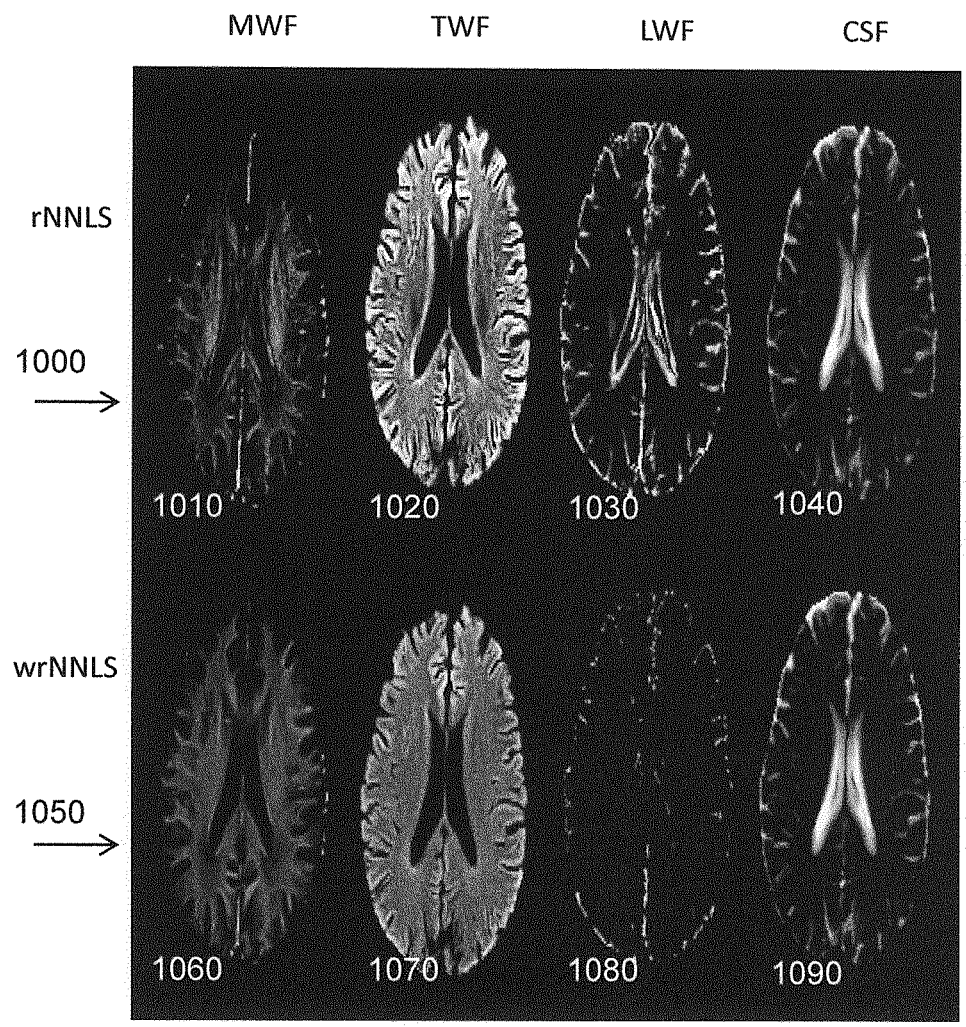
FIG. 10 illustrates images associated with non-weighted regularized $T_2$ spectral data and images associated with weighted regularized $T_2$ spectral data.

FIG. 10 illustrates images associated with non-weighted regularized spectral data and images associated with weighted regularized spectral data. Non-weighted parametric maps 1000 correspond to non-weighted MWF 1010, non-weighted TWF 1020, non-weighted LWF 1030, and non-weighted CSF 1040. The non-weighted parametric maps underestimate the non-weighted MWF 1010 near the edge of brain. Larger contamination in the non-weighted LWF map 1030 from the non-weighted CSF map 1040 is also visible because spectral amplitudes corresponding to larger $T_2$ value are overweighed in the regularization when using logarithmically spaced sampling.

The underestimation and contamination increased as the regularization constant increased. Accordingly, image quality of the non-weighted parametric maps 1000 was degraded and became unsuitable for assessing lesions in white matter. Weighted parametric maps 1050 correspond to weighted MWF 1060, weighted TWF 1070, weighted LWF 1080, and weighted CSF 1090. The weighted $T_2$SPARC method generated more uniform parametric maps than the non-weighted parametric maps 1000 as shown in FIG. 10.

Figure 11:
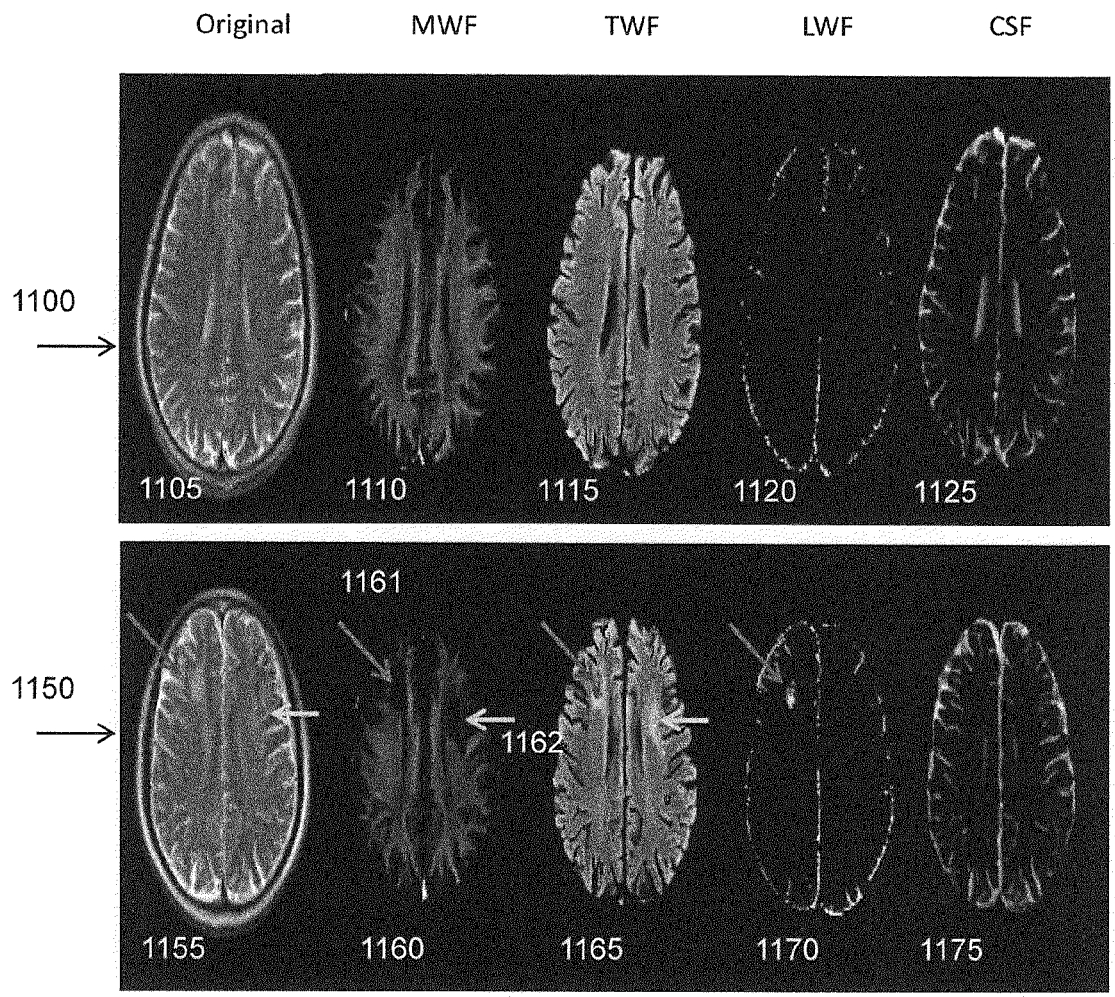
FIG. 11 illustrates images associated with a healthy brain and images associated with a brain affected by lesions.

FIG. 11 illustrates images associated a healthy brain and images associated with a brain having lesions. The healthy parametric maps 1100 correspond to healthy map 1105, healthy MWF 1110, healthy TWF 1115, healthy LWF 1120, and healthy CSF 1125. For comparison, diseased parametric maps 1150 are illustrated. The diseased parametric maps 1150 correspond to diseased map 1155, diseased MWF 1160, diseased TWF 1165, diseased LWF 1170, and diseased CSF 1175.

The difference in contrast in the diseased parametric maps 1150 to the healthy parametric maps 1100 indicates deviations in the corresponding fraction. For example, in the region of interest indicated by arrow 1161 in diseased MWF 1160 has an MWF of 1.9%. In the region of interest indicated by arrow 1162 in diseased MWF 1160 has an MWF of 4.5%. In the healthy MWF 1110, the corresponding regions of interest have an MWF of 12.3%. The differences in contrast of the healthy parametric maps 1100 and the diseased parametric maps 1150 make the regions of interest indicated by the arrows visually identifiable.

Figure 12:
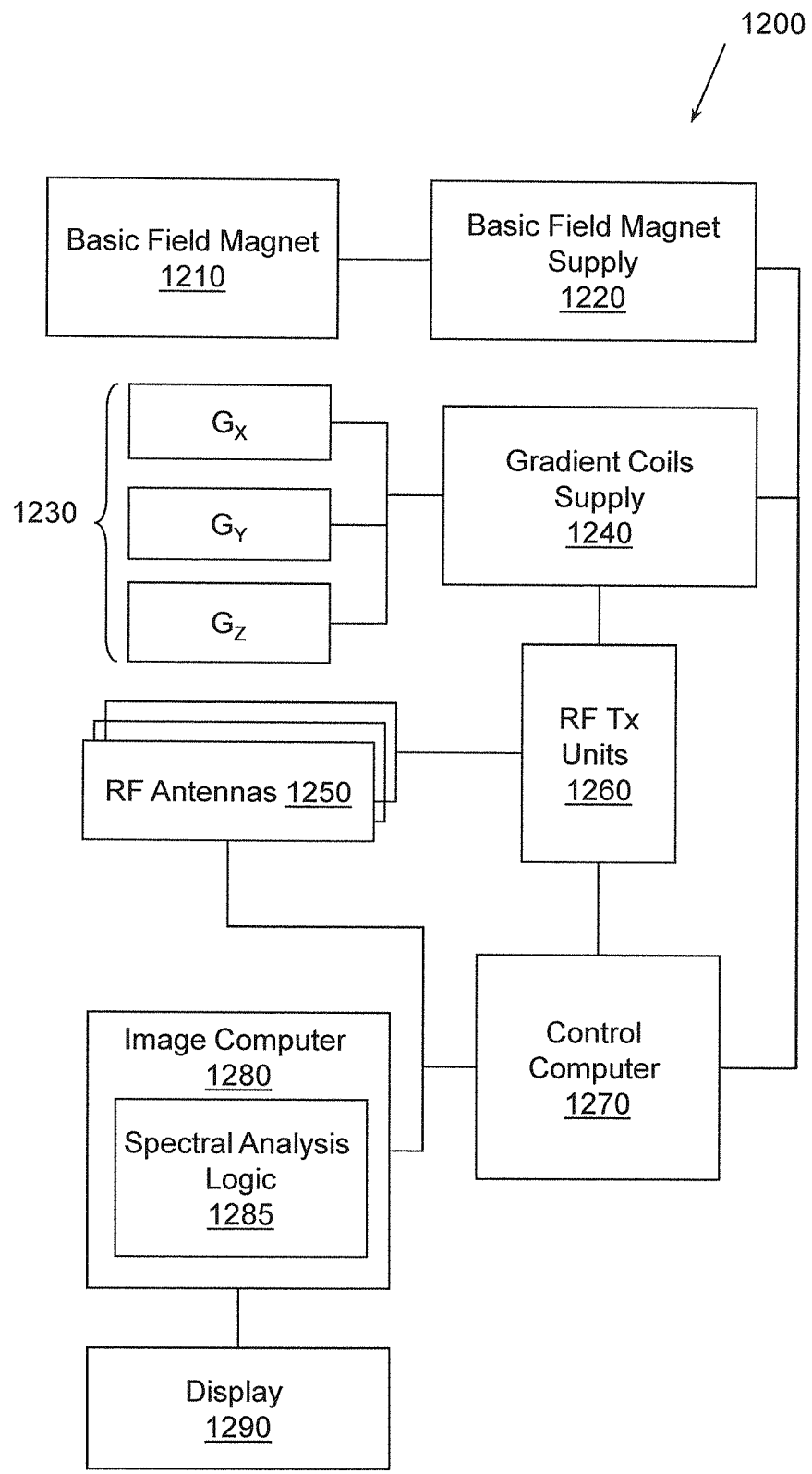
FIG. 12 illustrates an apparatus configured to perform spectral analysis of $T_2$ spectral data.

FIG. 12 illustrates an example MRI apparatus 1200 configured with a spectral analysis logic 1285. The apparatus 1200 includes a basic field magnet(s) 1210 and a basic field magnet supply 1220. Ideally, the basic field magnets 1210 would produce a uniform $B_0$ field. However, in practice, the $B_0$ field may not be uniform, and may vary over an object being imaged by the MRI apparatus 1200. MRI apparatus 1200 may include gradient coils 1230 configured to emit gradient magnetic fields like $G_S$, $G_P$ and $G_R$. The gradient coils 1230 may be controlled, at least in part, by a gradient coils supply 1240.

MRI apparatus 1200 may also include an RF antenna 1250 that is configured to generate RF pulses and to receive resulting magnetic resonance signals from an object to which the RF pulses are directed. In some examples, how the pulses are generated and how the resulting MR signals are received may be controlled and thus may be selectively adapted during an MRI procedure. In one example, separate RF transmission and reception coils can be employed. The RF antenna 1250 may be controlled, at least in part, by an RF transmission-reception unit 1260. The gradient coils supply 1240 and the RF transmission-reception unit 1260 may be controlled, at least in part, by a control computer 1270.

The magnetic resonance signals received from the RF antenna 1250 can be employed to generate an image, and thus may be subject to a transformation process like a two dimensional FET that generates pixilated image data. The transformation can be performed by an image computer 1280 or other similar processing device. The spectral analysis logic 1285 is configured to perform the methods described herein. The spectral analysis logic 1285 may include a filter logic to de-noise the pixilated image. The image data may then be shown on a display 1290. While an MR apparatus 1200 is illustrated, it is to be appreciated that in some examples the spectral analysis of spectral data may be employed with other imaging apparatus and/or methods (e.g., spectroscopy).

While FIG. 1200 illustrates an example MRI apparatus 1200 that includes various components connected in various ways, it is to be appreciated that other MRI apparatus may include other components connected in other ways. The spectral analysis logic 1285 may be configured with elements of example apparatus described to perform example method described herein.

In different examples, spectral analysis logic 1285 may be permanently and/or removably attached to an MRI apparatus. While spectral analysis logic 1285 is illustrated as a single logic connected to the image computer 1280, it is to be appreciated that spectral analysis logic 1285 may be distributed between and/or operably connected to other elements of apparatus 1200. Spectral analysis logic 1285 may execute portions of the methods described herein.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:
1. A method, comprising:
acquiring T2 spectral data from an object prepared by a pulse sequence applied by an MRI apparatus; and controlling a computer to perform a spectral analysis of the T2 spectral data, the spectral analysis comprising:
  decomposing the T2 spectral data with an integral using multi-exponential functions to determine T2 spectra;
  regularizing the T2 spectral data by applying a regularized constant, where the regularized constant is sufficiently large to smooth the T2 spectra so adjacent pixels of the T2 spectral data have characteristics that differ by less than a threshold amount;
  partitioning the T2 spectra into intervals by determining thresholds, where a threshold is defined by the T2 spectral data acquired in a predetermined time period, and where an interval corresponds to an individual spectrum; and
  generating at least one parametric map to correspond to at least one interval.

2. The method of claim 1, the spectral analysis further comprising weighting the multi-exponential function.

3. The method of claim 2, where the weighting is configured to be performed so that the regularization is uniformly weighted for the spectral amplitudes.

4. The method of claim 2, where the weighting is an inverse of log-spaced T2 time interval matrix.

5. The method of claim 1, where the pulse sequence comprises a refocusing slice and an excitation slice, and where the refocusing slice thickness is three times larger than the excitation slice thickness.

6. The method of claim 1, where the T2 spectral data was acquired over two interleaved scans, and where an interleaved scan acquires five slices.

7. The method of claim 5, where a slice gap between the five slices of a scan is based, at least in part, on an increased refocusing slice thickness.

8. The method of claim 1, where the intervals correspond to myelin water fraction (MWF), tissue water fraction (TWF), Long T2 water fraction (LWF), and cerebrospinal fluid fraction (CSF).

9. The method of claim 1, where regularizing the multi-exponential functions is performed according to a regularized non-negative least-squares approach.

10. The method of claim 1, where the regularized constant is in a range of 1.6 to 2.0.

11. The method of claim 7, where the time periods are based, at least in part, on T2 spectral data acquired at 3.0 Tesla, and correspond to the intervals: MWF having a time period of 0 ms-40 ms, TWF having a time period of 40 ms-200 ms, LWF having a time period of 200 ms-800 ms, and CSF having a time period of 800 ms-2000 ms.

12. The method of claim 1, where the spectral amplitudes are weighted equally.

13. The method of claim 1, where the filter is a nonlocal mean filter.

14. A non-transitory computer-readable medium storing computer-executable instruction that when executed by a computer control the computer to perform a method, the method comprising:
  decomposing T2 spectral data with an integral using multi-exponential functions to determine T2 spectra;
  regularizing the multi-exponential functions by applying a regularized constant, where the regularized constant is sufficiently large to smooth the T2 spectra so adjacent pixels of the T2 spectral data are similar to within a threshold amount;
  partitioning the T2 spectra into intervals by determining thresholds, where a threshold is defined by the T2 spectral data acquired in a predetermined time period, and where an interval corresponds to an individual spectrum; and
  generating a parametric map to correspond to at least one interval.

15. The non-transitory computer readable medium of claim 14, the method further comprising:
  weighting the T2 spectral data so that the regularization is weighted to within a desired uniformity for the spectral amplitudes.

16. The non-transitory computer readable medium of claim 14, where an inverse of log-spaced T2 time interval matrix is applied to the T2 spectral data.

17. The non-transitory computer readable medium of claim 14, where the at least one interval corresponds to myelin water fraction (MWF), tissue water fraction (TWF), Long T2 water fraction (LWF), and cerebrospinal fluid fraction (CSF).

* * * * *

UNITED STATES PATENT AND TRADEMARK OFFICE
CERTIFICATE OF CORRECTION

PATENT NO.         : 9,378,548 B2                                                Page 1 of 1
APPLICATION NO.    : 14/359722
DATED              : June 28, 2016
INVENTOR(S)        : Junyu Guo et al.

It is certified that error appears in the above-identified patent and that said Letters Patent is hereby corrected as shown below:

In the Specification

Column 1, Line 3 should read:
This invention was made with government support under grant number CA090246 awarded by the National Institutes of Health. The government has certain rights in the invention.

Signed and Sealed this
Thirty-first Day of March, 2020

Andrei Iancu
*Director of the United States Patent and Trademark Office*